United States Patent [19]
Olovson

[11] Patent Number: 5,141,495
[45] Date of Patent: Aug. 25, 1992

[54] SYRINGE

[76] Inventor: Gudmar Olovson, 64, rue Saint-Charles, 75015 Paris, France

[21] Appl. No.: 689,897
[22] PCT Filed: Dec. 11, 1989
[86] PCT No.: PCT/SE89/00722
  § 371 Date: Jun. 14, 1991
  § 102(e) Date: Jun. 14, 1991
[87] PCT Pub. No.: WO90/06785
  PCT Pub. Date: Jun. 28, 1990

[30] Foreign Application Priority Data

Dec. 14, 1988 [SE] Sweden ............... 8804523

[51] Int. Cl.$^5$ .................................... A61M 5/00
[52] U.S. Cl. .................................... 604/110; 604/218
[58] Field of Search ............. 604/110, 218, 187, 263, 604/220, 221, 228, 230

[56] References Cited

U.S. PATENT DOCUMENTS

| | | |
|---|---|---|
| 4,391,272 | 7/1983 | Staempfli . |
| 4,699,614 | 10/1987 | Glazier . |
| 4,775,364 | 10/1988 | Alles . |
| 4,813,940 | 3/1989 | Parry . |
| 4,826,483 | 5/1989 | Molnar, IV .................... 604/110 |
| 5,032,114 | 7/1991 | Olovson . |

FOREIGN PATENT DOCUMENTS

| | | |
|---|---|---|
| 0229017 | 7/1987 | European Pat. Off. . |
| 2613628 | 4/1987 | France . |
| 413838 | 6/1980 | Sweden . |
| 438598 | 4/1985 | Sweden . |
| 505625 | 5/1971 | Switzerland . |
| 2197792A | 6/1988 | United Kingdom . |
| WO88/02640 | 4/1988 | World Int. Prop. O. . |

Primary Examiner—John D. Yasko
Attorney, Agent, or Firm—Burns, Doane, Swecker & Mathis

[57] ABSTRACT

The disclosure refers to a syringe, comprising a container, a needle, capable of co-acting with one end container, a plunger which is located inside the container and which co-acts sealingly with the inner surface thereof, and shaped element which coacts with the plunger and which is arranged for rectilinear reciprocating movement relative to the container. There being provided means which takes an inactive state, in which co-action between the rod-shaped element at the plunger is discontinued, therewith to prevent further liquid from being drawn into the container upon renewed line movement of the rod-shaped element in a first direction. The plunger or a part thereof is intended to take a position which the plunger is effective to prevent the container from being filed with injection liquid via the needle or its attachments means.

6 Claims, 2 Drawing Sheets

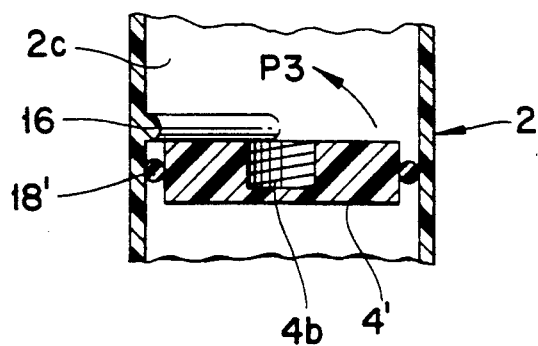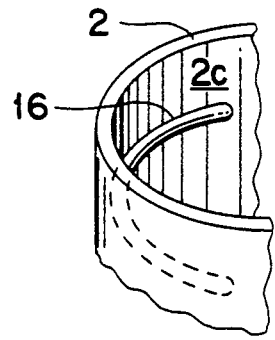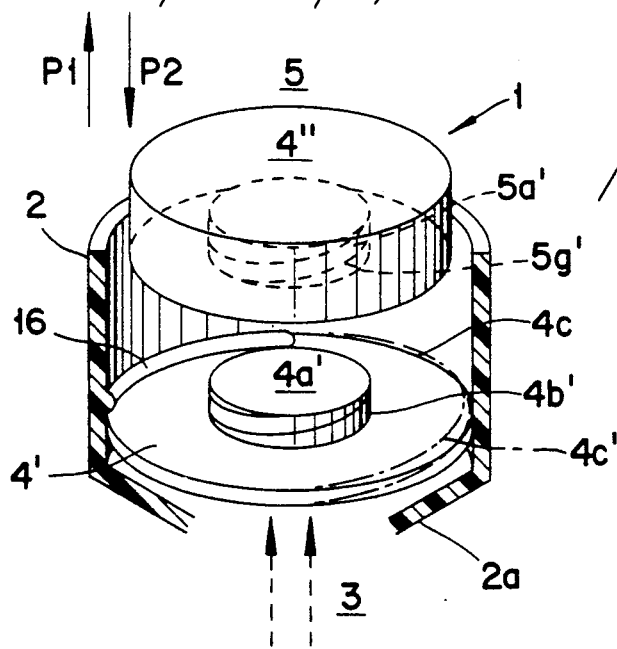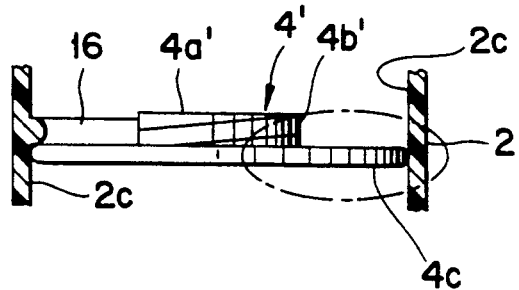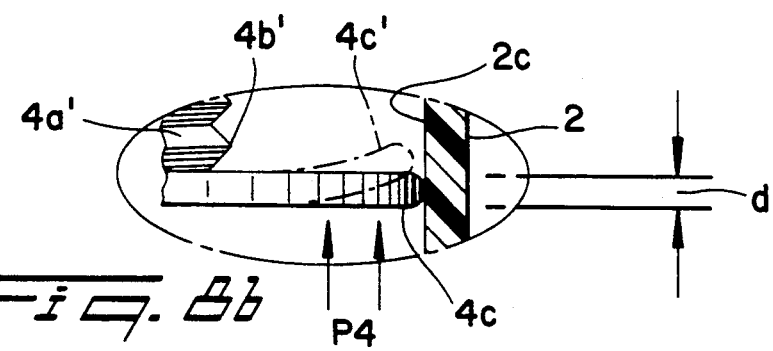

SYRINGE

TECHNICAL FIELD

The present invention relates to a syringe, and more particularly, but not exclusively, to a hand-operated syringe of the kind which comprises a container, a needle which is adapted to cooperate with one end of the container, a plunger which is adapted to be located inside the container and which is intended to co-act sealingly with the inner surface thereof, and a rod-shaped element, which is arranged to co-act with the plunger for a reciprocating plunger movement in said container. The rod-shaped element is capable of being displaced rectilinearly relative to the container, such that linear movement of said element in a first direction, from said one end, causes the container to be filled with liquid intended for subsequent injection, while linear movement of the element in a second direction causes the liquid to be emptied from the container through the needle during injection.

The present invention is concerned primarily with a disposable-type syringe or a non re-usable disposable hypodermic syringe, by which is meant, a syringe whose container can be filled with injection liquid only- .once, i.e. after being once filled it can hardly be filled again and if it is filled the re-filled liquid can not be pressed through the needle for injection by any movement of the rod-shaped element.

BACKGROUND PRIOR ART

Several variants of syringes of this kind are known to the art.

In a first re-usable variant of these known syringes, the mutual co-action of the plunateger and the rod-shaped element is facilitated with the aid of means located between said plunger and said element, this means holding the plunger to the rod-shaped element during linear movement of the element in said first direction and also during linear movement of the element in said second direction. Thus, there is no detachable connection between the plunger and the rod-like element and the plunger will thus be moved backwards and forwards in the container in precise response to the direction of movement of the rod-shaped element.

This means that the container can be filled with liquid each time the plunger is moved away from the needle, and emptied of liquid each time the plunger is moved towards the needle, thereby enabling the syringe to be used over and over again.

The repeated use of one and the same syringe has proven to constitute a serious risk of spreading disease, such as AIDS.

Consequently, single-shot syringes or non re-usable disposable hypodermic syringes have been proposed, which can be used only once for injection purposes, after which the container can no longer be filled with liquid for subsequent injection.

An example of a first variant of such a previously known single-shot syringe is described and illustrated in European Patent Application Ser. No. 0 229 017, in which syringe, the plunger, and a rod-shaped element co-act with one another through the intermediary of hook-shaped members, which are moved out of engagement with the plunger upon movement of the rod-shaped element towards the needle.

The Swedish Patent Specification Publ. No. 413 838 describes and illustrates another variant, a so-called single-shot syringe in which the rod-shaped element incorporates a weakening at a location adjacent the plunger, and in which means are provided for twisting the element relative the plunger subsequent to completing an injection, thereby fracturing the rod-shaped element at the weakened location.

The Swedish Patent Specification Publ. No. 438 598 also teaches a single-shot, or disposable syringe, in which is disclosed in the container a circular groove adapted to cooperate with an outstanding part of the plunger for locking the plunger in its end-position and thus preventing re-filling through the needle.

A similar syringe design is shown in the International Publication WO88/02640.

Finally the syringe, of single-shot type, shown and described in the U.S. Pat. No. 4,699,614 belongs to the prior art and has a freely rotatable arm arranged to follow or slip a guide track, causing an attempt to move the plunger once again away from the needle, for the purpose of filling the container with liquid, to fail, as the plunger and the rod-shaped element no longer are co-acting with each other.

A re-filling through the needle is here possible.

SUMMARY OF THE INVENTION

Technical Problems

When viewing the prior art it will be seen that a technical problem is one of providing a syringe which can be filled with injection liquid in a conventional manner and in which, when the plunger is moved by the rod-like element a short distance towards the needle, there is activated a means which renders it impossible to refill the container with liquid, since the ability of the syringe to draw in liquid by suction is placed out of function, regardless of how careful the plunger is moved towards the needle, and furthermore cause such conditions that the container can hardly be filled with injection liquid via the needle or its attachment means, when said liquid is placed under pressure for the purpose of filling the container or if the container, in spite of these conditions, is filled with injection liquid via the needle, the rod-like element, when moved towards the needle, cannot cause the filled injection liquid to pass through the needle.

It will also be seen that a technical problem, when considering a solution to the above mentioned technical problem, is one of providing simple designs of each part used and in addition to that provide a syringe, which comprises only a few parts.

A further technical problem is one of realizing the possiblities which are afforded when the plunger or a part thereof can be locked, in a position in which it is located close to the needle, and when located in this position, it cannot be moved therefrom, but a part thereof can be bent, when liquid under overpressure acts upon the under surface of the plunger, via the needle causing the liquid to pass to the space above the plunger.

Another technical problem is one of realizing the possibilities which are afforded when also the rod-shaped element can be locked firmly in a position close to the needle.

Solution

While taking into consideration the earlier prior art and with consideration of the aforesaid technical problems, the present invention relates to a syringe, which comprises; a container, a needle, which cooperates with one end of the container, a plunger, which is located inside the container and which sealingly co-acts with the inner surface thereof, and a rod-shaped element, which co-acts with the plunger and which is arranged for linear movement relative to the container such that linear movement of said element in a first direction from said one end will cause the container to be filled with injection liquid, while linear movement of the element in a second direction, opposite to said first direction, causes the liquid to be emptied from the container through the needle.

The invention is further based on a syringe of the kind, in which there is provided, between the plunger and the rod-shaped element, means which hold the plunger firmly to the rod-shaped element when the element is moved linearly in said first direction.

The invention is also based on a disposable, or single-shot, syringe of the kind, in which upon displacement of the rod-shaped element and the plunger in the opposite direction the aforesaid means is brought to an inactive position, in which it discontinues the co-action between said element and the plunger, such that no injection liquid will be drawn into the container upon further linear movement of said element in the first direction.

The present invention discloses, as a development of the above-mentioned single-shot syringe, that the plunger or a part thereof is intended to take a position in which the plunger is effective to prevent the container from being filled with injection liquid through the needle or its attachment means or that the plunger or a part thereof may also cooperate with means effective to bring the plunger or a part thereof into an inactive sealing position by said pressurized injection liquid acting on the plunger or a part thereof when passing through the needle.

In accordance with a preferred embodiment, which falls within the scope of the present invention, it is suggested that the plunger will cooperate with first means, such as to lock the plunger in a predetermined position.

According to another variant the rod-shaped element is arranged to cooperate with means, such as to lock the element in a predetermined position.

According to an embodiment, particularly preferred, said means shall have the form of a rim or edge, which extends into the container and which is positioned on the inner surface of the container and arranged at one side thereof and located, behind the plunger, as seen from the needle, whereby the plunger has sufficient dimension along the container to clamp the plunger via its edges.

The second means, particularly preferred, may have the form of a rim or edge, which extends into the container and which is positioned on the inner surface of the container and arranged at one side thereof and located behind the plunger, as seen from the needle, whereby the plunger has a restricted extension or dimension along the container so that the plunger can be tilted or a part thereof bent from a sealing or active position to a non-sealing or in-active position by the pressure of the liquid.

The third means has the form of an edge, which is positioned on the inner surface of the container and which is arranged on one side thereof, adapted to lock the rod-shaped element, should said element be moved in a direction away from the needle once again.

It is also suggested that the element is arranged to turn together with said plunger in a first direction relative said container when said element is moved in a direction of movement out of said container and to turn in a opposite direction, while the plunger is disconnected from the element, when said element is pressed a short distance into the container.

The element is adapted to turn in a right-hand-threaded direction when said element is moved in a direction out of the container. The plunger is connected to said element by a left-hand-threaded connection.

It is also possible to form said second means as a groove positioned on the inner surface of the container and arranged at one side thereof and located close to the plunger, having a restricted extension or dimension along the container so the plunger can be tilted or a part thereof bent from a liquid sealing or active position to a non-sealing or in-active position by the pressure of the liquid.

Advantages

The advantages primarily afforded by a syringe according to the present invention reside in the possibility of providing, in a simple fashion, a disposable syringe with which the syringe container practically can be filled with injection liquid only once, by moving the rod-shaped element in a direction away from the needle, and with said element the container can be emptied, or substantially emptied, of liquid only once, by moving the rod-shaped element in a direction towards the needle and with which the ability of the container to take in liquid is placed out of function, even if measures are taken to prevent this from happening, thereby rendering refilling of the container more or less impossible. Furthermore it is hard to refill the container by using pressurized liquid and trying to fill the container via said needle or its attachment means for a subsequent injection, and if, in spite of that, filled or partly filled with injection liquid no injection will occur by a removement of the rod-shaped element towards said needle.

BRIEF DESCRIPTION OF THE DRAWINGS

Preferred embodiments of syringes, constructed in accordance with the present invention, will now be described in more detail with reference to the accompanying drawings, in which;

FIG. 5 is a sectional view of the lowermost part of the container with a plunger or a plunger part located in said part, FIG. 6a is a perspective view of a rim or edge, formed on a part of the inner surface of the container's lowermost part, FIG. 6b is a detail in cross-section of a portion of FIG. 6a, FIG. 7 is a perspective view of an embodiment having a two-part plunger design, FIG. 8a is illustrating the function of the lower part of the plunger design shown in FIG. 7, FIG. 8b is an enlarged detail of a portion of FIG. 8a.

DESCRIPTION OVER NOW PREFERRED EMBODIMENT

Figure 1:
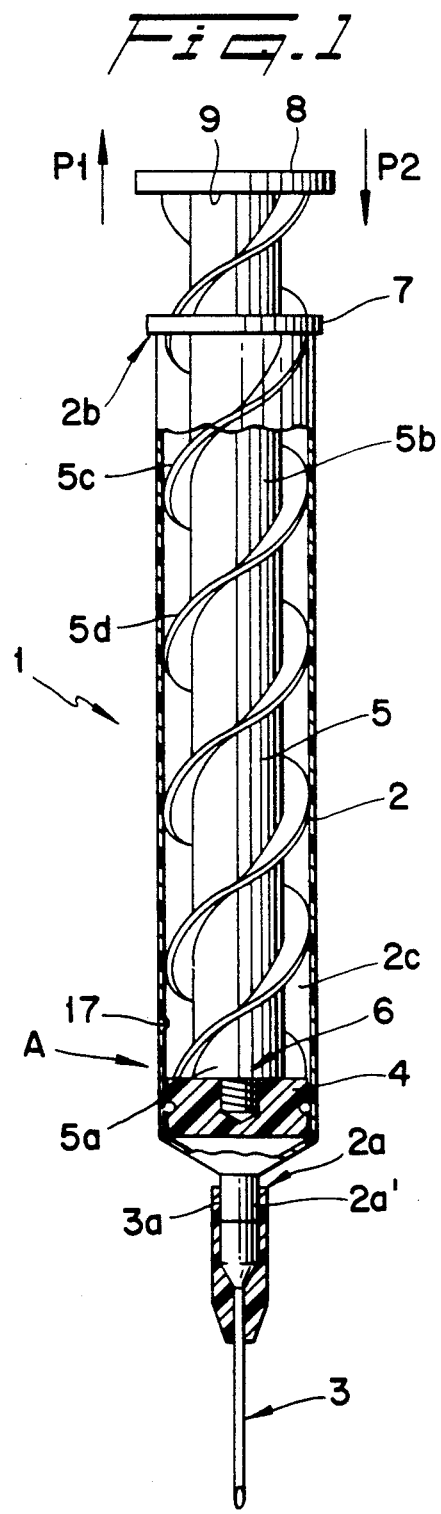
FIG. 1 is a partially sectioned side view of a syringe showing means significant of the invention and acting between a plunger and a rod-shaped element in an active position.

In FIG. 1 there is illustrated a syringe 1, a hypodermic syringe, which comprises a container 2 having a needle 3, which cooperates with one end 2a of the container and which is provided with an inner, conical socket-like member 3a, intended to embrace an outer conical peg 2a' in a known manner.

The syringe illustrated in FIG. 1 also includes a one-part plunger 4, which in the illustrated embodiment is shown fully depressed in the container 2 and which is intended to co-act sealingly with the inner surface 2c of the container 2. Co-acting with the plunger 4 is a rod-shaped element 5, which can be displaced linearly by hand in relation to the container 2 such as to move the element in a first direction "P1" away from said one end 2a, therewith to fill the container 2 with injection liquid, and in a second direction "P2" towards said one end 2a, therewith to eject the liquid in the container through the needle 3, there being provided between the plunger 4 and the element 5, at the end 5a of said element, a means 6, which is operative in providing this particular co-action between said plunger and said element and which holds the plunger 4 firmly to the element 5 during movement in the first direction "P1". During this first movement, the container 2 is filled with liquid as a result of the partial vacuum prevailing in the container.

Figure 2:
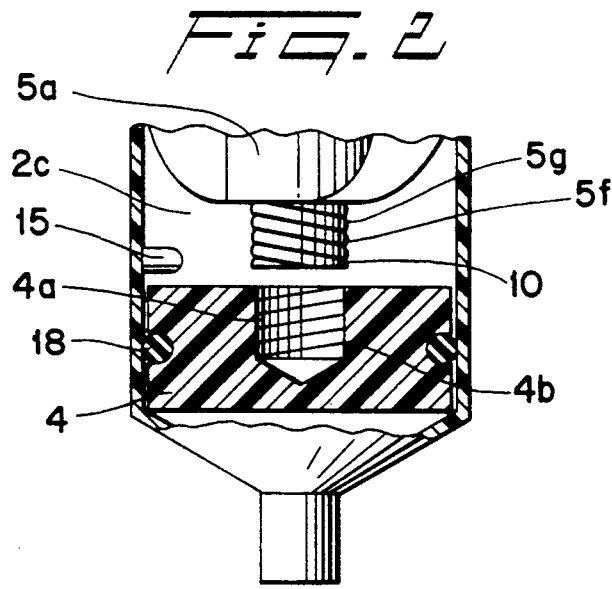
FIG. 2 is a side view in a larger scale of the aforesaid means in an inactive position.

It is suggested that the means 6 is brought to an inactive position, shown in FIG. 2, when the rod-shaped element 5 and the plunger 4 are moved a short distance in the opposite direction "P2", such as to discontinue the mutual co-action between the element 5 and the plunger 4. As a result thereof no injection liquid will be drawn into the container 2 when the rod-shaped element 5 is again moved in the first linear direction "P1", since the one-part plunger 4 is unable to accompany the element 5.

This inactive position of the means 6 is obtained immediately, and the plunger 4 and the element 5 are stopped and urged slightly in the opposite direction.

With regard to the means 6 and the element 5, said element, when moved in the direction "P1", will rotate together with the plunger 4 in the direction of the right-hand screwthread. The element 5 and the plunger 4 co-act with one another through the intermediary of a screwthread (left-hand screwthread).

This rotational movement of the element 5 is achieved through the particular construction of said element. Thus, the element 5 comprises an inner rod 5b having provided thereon two right-hand helical lands 5d, which form a screwthread having two leads and a large pitch.

Figure 4:
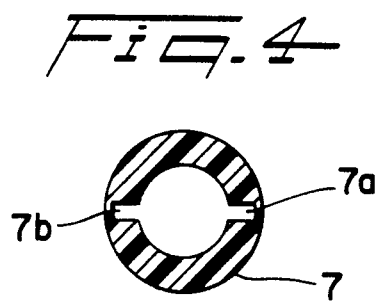
FIG. 4 is a cross-sectional view of an upper container cover plate, which is intended to rotate the rod-shaped element about its longitudinal axis in response to linear movement of said element.

It will be seen from FIG. 4 that the land or projection 5c is intended to co-act with a recess or cut-out 7a in an upper container cover-plate 7, whereas the land or projection 5d is intended to co-act with a recess or cut-out 7b. The syringe also includes an upper plate 8, which is rotatably connected to the element 5 through the intermediary of a rotational shaft 9 in a known manner.

The advantage with this embodiment is that the lands 5c and 5d need not connect with the inner surface of the container, but can be made narrower.

As will be seen from FIG. 2, the plunger 4 is provided wich a screwthreaded hole 4a provided with a screwthread 4b, and that the end 5a of the rod-shaped element 5 has a peg 5a, which is provided with a corresponding screwthread 5g.

Figure 3:
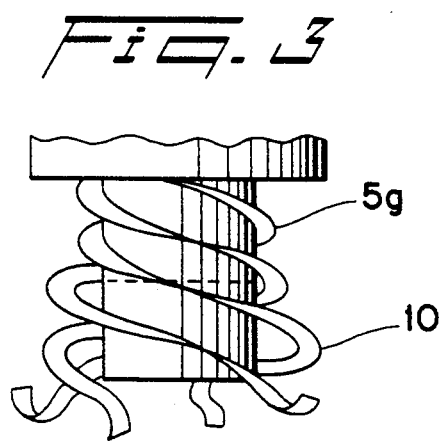
FIG. 3 illustrates one embodiment of a catch means in larger scale than that of FIG. 2.

The screwthreads 4b and 5g are left-hand screwthreads and in practice the pitch of the threads is much larger than that shown in FIGS. 2 and 3.

In case of the illustrated embodiment, linear movement of the element 5 in the direction of the arrow "P1" will result in clockwise rotation of the element 5, whereas the left-hand screwthread of the plunger 4 ensures that the plunger is held to the lower part 5a of the element 5.

As soon as this movement stops and the element is moved linearly and rotated in the direction of arrow "P2", the plunger 4 will be unscrewed from the element 5. This discontinuation of the co-action between said plunger and said element takes place after only a short distance. As will be understood, the plunger 4 shall not rotate together with the element 5. Consequently, the container may be given a slightly eliptical cross-sectional shape.

As an alternative embodiment, the rotational movement imparted by the element 5 during its linear movement from a position shown in FIG. 1 as "A" to a position in which the part 5a is located in the illustrated position is sufficient for a right-hand screwthread 5g on the peg 5a to be moved out of co-action with the thread 4b in the recess 4a.

The screwthreads 5g and 4b may have three or four leads.

It is a prerequisite of the function that linear movement of the element 5 will positively result in rotational movement relative to the element 5 and the plunger 4, and consequently, it is suggested that the container 2 is given a cross-sectional shape, which deviates from a circular line, and that the plunger 4 is optionally given a shape adapted thereto, thereby making it more difficult to rotate the plunger 4 relative to the container 2 than the element 5.

The extent to which the cross-sectional shape of the container shall deviate from a circular line depends upon the material from which the plunger 4 is made and on how readily the screwthread 5g co-acts with the screwthread 4b.

This description is limited to the illustration of solely one example of how a desired co-action between the plunger 4 and the rod-shaped element 5 is achieved.

Alternative embodiments, however, also lie within the purview of the present invention.

A number of different, suitable, embodiments are described and illustrated in the International Patent Application PCT/SE88/00634.

As previously stated, a plate or cover 7 co-acts with the other or upper end 2b of the container 2. This cover plate is welded to the container 2 or secured thereto in some other known manner, and presents grooves or slots 7a, 7b, by means of which the rod-like element 5 is caused to rotate about its longitudinal axis to an extent corresponding to the linear movement of said element. This cover plate is affixed to the container subsequent to the element 5 and the plunger 4 is inserted into the container 2, in their mutually co-acting state.

The element 5 presents a helical configuration with two leads having a central part, although the element may alternatively be given a rectangular cross-sectional shape to which a helical configuration is subsequently imparted.

It is essential that when the mutual coaction between the plunger 4 and the element 5 is discontinued, as shown in FIG. 2, a catch means 10 can be inserted between the screwthreads, thereby preventing the screwthread 5g from being re-screwed into the screwthread 4b. The catch means 10 is shown in FIG. 3 and comprises a helical wire, which is arranged to the lower part of the screwthread 5g and which in a free position forms a stop against co-action between the screwthreads 5g and 4b.

The catch wire 10 may have a screwthread-form so that it is able to co-act with the screwthread 4b and, when said co-action is discontinued, to take a helical form around the peg 5f, thereby making renewed co-action between the screwthreads 5g and 4b impossible.

Other embodiments of such catch means are also conceivable.

All of the syringe components, possibly with the exception of the plunger 4, are preferably manufactured from a suitable plastic material. The plunger may be a resilient piston, made of a medical rubber compound.

It is also proposed that the pitch of the screwthreads 5c and 5d is adapted to the pitch of the screwthreads 5g and 4b, so that the plunger 4 will discontinue its coaction with the rod-shaped element 5 when the element is moved linearly through a distance of less than 10% of the possible maximum distance, preferably less than 5% of said maximum distance.

The shorter the linear distance moved, the better the technical advance.

In order to inhibit the practical possibility of re-filling the container, to fill the space between the plunger and the needle, for instance by pressing a liquid through said needle or its attachment means, with the aid of a pressurized liquid, means are proposed whereby said element, and preferably said plunger, is moved to a position by said pressure in which a re-filling of the container in this manner is hard and if said space is filled said element 5 or said plunger 4 cannot press the liquid through the needle 3.

This can be achieved in accordance with the following;
a) lock the plunger 4 or a part thereof against movement away from the needle in a predetermined end-position,
b) cause the plunger or a part thereof to move out of a sealing position towards the inner surface of the container by said pressure and,
d) lock the element 5 against movement away from the needle.

In accordance with the invention, the plunger 4 shall be able, upon an initial movement away from the needle 3, to co-act with first means 15, which lock the plunger and its movement in a predetermined position or to co-act with second means 16, which causes a part of the plunger to move out of its sealing position upon said movement away from the needle 3.

Further, it is suggested that the element 5 also shall be able to co-act with a third means 17, which locks the element in a predetermined position.

Said first means 15 will preferably have the form of a rim or edge, which extends into the container and which is positioned on the inner surface 2c of the container and arranged at one side thereof and located, behind the plunger, as seen from the needle, whereby the plunger 4 has sufficient dimension along the container so the plunger 4 can be clamped in a tilted position via its edges.

The second means 16 may have the form of a rim or edge, which extends into the container and which is positioned on the inner surface 2c of the container 2 and arranged at one side thereof and located behind and adjacent the plunger, as seen from the needle, whereby the plunger 4' (FIG. 5) has a restricted extension or dimension along the container so the plunger can be tilted, as seen in the arrow P3, from a sealing or active position to a non-sealing or in-active position.

The third means 17 has the form of an edge, which is positioned on the inner surface of the container and which is arranged at one side thereof, adapted to lock the rod-shaped element, should said element again be moved in a direction away from the needle.

It is suggested that the element 5 is arranged to turn together with said plunger in a first direction relative said container when said element is moved in a direction out of said container and turn in a opposite direction, while the plunger is disconnected from the element, when said element is pressed a short distance into the container.

The means 15, 16 and 17 are identical.

In the case when the container 2 has a slightly elliptic cross-section, the means 16 will have a form whereby said cross-section will adapt more to a complete circular form.

The junction shall be smooth, causing said plunger 4 and its sealing means 18' to pass over said means 16 with acceptable sealing effect.

It is suggested that said means 16 has a wrap-area of between 90° and 180°, preferably about 100°.

The means 17 is so positioned that when turned once, in order to lift the plunger, no cooperation takes place but when the plunger 4 and the element 5 are spaced apart, as shown in FIG. 2, the means 17 will be pressed towards the aforesaid lands or projections 5d.

The means 17 may be applied as separated projections along the whole length of the container.

The means 15 and 16 may also be in the form of a groove, into which plunger-sealing means will fit.

In the case of the FIG. 2 embodiment, the plunger 4 is relatively thick and when the plunger is raised to an extend at which the seal 18 abuts the edge 15, the plunger will be tilted anti-clockwise and clamped between the inner surface of the container by opposing edges.

In the case of FIG. 5 embodiment it is shown that the plunger 4' is so thin that when the plunger is raised to an extent at which the seal 18' abuts the edge 16, the plunger 4' will tilt anti-clockwise and turned from an active-sealing position into an inactive-non-sealing position and will relinquist its sealing engagement with the inner surface 2c of the container 2.

Referring to the last shown embodiment, in FIGS. 7 and 8, it is suggested that the plunger is formed as a two-part-plunger, an upper part 4", with a non-sealing cooperation with the inner surface 2c of the container 2, and a lower part 4', with a sealing cooperation with the inner surface 2c of the container 2.

The upper part 4" is of plastic material and can be a part of the end 5a of the element 5 and is rigid and is cooperating with the lower part 4' over a threaded recess-portion 5a' and a peg-portion 4a' as described above.

The lower part 4' is made of a flexible rubber or plastic material, of the kind already used as plungers in syringes of previously known designs.

It is here suggested that the used thread 4b' shall have a diameter more than 20% and less than 80% of the diameter of the container 2, preferably between 40 and 60%.

It is here further suggested that the thickness "d" of the lower part 4' is 0,5–4,0 mm, depending upon the size of the container and the diameter of the threaded part 4a'.

In this embodiment it is suggested that the lower elastic sealing part 4' has an upstanding peg 4a', instead of a recess, with a screwthread 4b'.

When this lower elastic and sealing part 4', at the end of the injection sequence, passes the means 16, in the form of an half-circular rim or edge, this lower part 4' is locked at one side only.

When attempts are made for re-filling the container 2, by pressing a liquid under pressure "P4" through the needle 3 or its attachments means, the half-circular surface 4c of the elastic and sealing part 4', not in co-operation with the rim 16, will be bent slightly upwardly, by the pressurized liquid, to a non-sealing position 4c', causing said liquid to pass around said lower part 4' into the space above the lower part. This quantity cannot be pressed through the needle 3 by any movement of the upper part 4" or the element 5 as this movement firstly causes the lower part 4' to return from its non-sealing position 4c' to its sealing position 4c and secondly the upper part 4" is not in a sealing cooperation with the inner surface 2c of the container 2 and connot, by any movement towards the needle 3, press said by-passed liquid under pressure through the needle 3 for injection.

It is suggested that the part 4' is, in the position shown in FIG. 7, resting towards a circular supporting and sealing surface.

It will be understood that the invention is not restricted to the aforedescribed embodiments, and that modifications can be made within the scope of the following claims.

I claim:

1. A syringe (1) comprising a container (2), a needle (3) capable of co-acting with one end (2a) of the container, a plunger (4) which is located inside the container and which co-acts sealingly with the inner surface thereof (2), and a rod-shaped element (5) which co-acts with the plunger and which is arranged for rectilinear reciprocating movement relative to the container, such that linear movement of said element in a first direction (P1) from said one end (2a) causes the container to be filled with liquid to be injected, while linear movement of the element in a second direction (P2) causes the liquid to be emptied from the container (2) through the needle (3), there being provided between the plunger (4) and the rod-shaped element (5), for their mutual co-action, a means (6) which during linear movement of said element in said first direction (P1) holds the plunger (4) against the rod-shaped element (5) and which upon linear movement of the element (5) and the plunger (4) in the opposite direction (P2) takes an inactive state, in which co-action between the rod-shaped element (5) and the plunger (4) is discontinued, therewith to prevent further liquid from being drawn into the container upon renewed linear movement of the rod-shaped element in the first direction (P1), characterized in that the plunger is intended to co-act with means (16) bringing the plunger or a part thereof into an in-active sealing position by a pressurized injection liquid via the needle (3) or its attachment means.

2. A syringe according to claim 1, characterized in that said means (16) has the form of a rim or edge, which extends into the container and which is positioned on the inner surface of the container and arranged at one side thereof and located behind the plunger, as seen from the needle, whereby the plunger has a restricted extension or dimension along the container so the plunger (4) can be tilted or a part thereof bent from a sealing or active position to a non-sealing or in-active position by the pressure of said liquid.

3. A syringe according to claim 1, characterized in that the element (5) is arranged to turn together with said plunger (4) in a first direction (P1) relative said container when said element is moved in a direction out of said container and turn in a opposite direction, while the plunger (4) is disconnected from the element (5), when said element (5) is pressed a short distance into the container.

4. A syringe according to claim 1, characterized in that said element (5) is adopted to turn in a right-hand-threaded direction when said element (5) is moved in a direction out of the container (2) and that said plunger (4) is connected to said element by a left-hand-threaded connection.

5. A syringe according to claim 1, characterized in that said means (16) has the form of a groove positioned on the inner surface of the container and arranged at one side thereof and located close to or adjacent the plunger (4), whereby the plunger (4') has a restricted extension or dimension along the container (2) so the plunger (4') can be tilted or a part thereof be bent from a sealing or active position to a non-sealing or in-active position by the pressure of the liquid.

6. A syringe according to claim 3, characterized in that said element (5) is adapted to turn in a right-hand-threaded direction when said element (5) is moved in a direction out of the container (2) and that said plunger (4) is connected to said element by a left-hand-threaded connection.

* * * * *